(12) United States Patent
de Bondt et al.

(10) Patent No.: US 8,549,926 B2
(45) Date of Patent: Oct. 8, 2013

(54) TESTING APPARATUS

(75) Inventors: Adriaan Hermann de Bondt, Nieuwegein (NL); Radjan Nerinderpersad Khedoe, The Hague (NL); Frederik Roelf Spieard, Avenhorn (NL)

(73) Assignee: Ooms Civiel B.V., Scharwoude (NL)

( * ) Notice: Subject to any disclaimer, the term of this patent is extended or adjusted under 35 U.S.C. 154(b) by 230 days.

(21) Appl. No.: 13/112,336

(22) Filed: May 20, 2011

(65) Prior Publication Data

US 2011/0303018 A1 Dec. 15, 2011

(30) Foreign Application Priority Data

May 20, 2010 (NL) ..................................... 2004751

(51) Int. Cl.
*G01B 5/30* (2006.01)
*G01N 3/08* (2006.01)

(52) U.S. Cl.
USPC .............................................. 73/760; 73/818

(58) Field of Classification Search
USPC .............................. 73/760, 862.392, 803, 818
See application file for complete search history.

(56) References Cited

U.S. PATENT DOCUMENTS

| | | | |
|---|---|---|---|
| 3,119,257 A | | 1/1964 | Speer |
| 4,502,327 A | * | 3/1985 | Scrivener et al. ................ 73/146 |
| 4,887,463 A | * | 12/1989 | Wood ............................... 73/146 |
| 4,938,055 A | | 7/1990 | Tsuda |
| 5,281,535 A | | 1/1994 | Wei et al. |
| 5,481,907 A | | 1/1996 | Chasco et al. |
| 5,659,140 A | | 8/1997 | Jakob et al. |
| 5,969,261 A | | 10/1999 | McAlister et al. |
| 6,276,189 B1 | * | 8/2001 | Hurson ................................ 73/9 |
| 6,427,528 B1 | * | 8/2002 | Yamakado et al. ............. 73/121 |
| 6,510,733 B2 | * | 1/2003 | Coe et al. ......................... 73/146 |
| 6,513,384 B1 | | 2/2003 | Quibel et al. |
| 6,928,857 B1 | * | 8/2005 | Brown ................................ 73/9 |
| 7,082,839 B2 | | 8/2006 | Pyle et al. |
| 7,197,920 B2 | * | 4/2007 | Friske et al. .................... 73/146 |

FOREIGN PATENT DOCUMENTS

| | | |
|---|---|---|
| EP | 1063517 A1 | 12/2000 |
| EP | 1081484 A2 | 3/2001 |
| EP | 1931966 A1 | 6/2008 |
| GB | 460001 | 1/1937 |
| GB | 609369 | 9/1948 |
| GB | 1602700 | 11/1981 |
| GB | 2104010 | 3/1983 |
| GB | 2135944 | 9/1984 |
| JP | 61080025 | 4/1986 |
| JP | 10038791 | 2/1998 |
| JP | 2005315594 | 11/2005 |
| JP | 2008-209399 | 9/2008 |
| JP | 2010-216866 | 9/2010 |
| WO | WO 2007/040409 A1 | 4/2007 |

OTHER PUBLICATIONS

Dutch Search Report dated Jan. 20, 2011, from NL 2004751.

\* cited by examiner

*Primary Examiner* — Max Noori
(74) *Attorney, Agent, or Firm* — Swanson & Bratschun, L.L.C.

(57) ABSTRACT

A testing apparatus is provided that includes a carrying construction for supporting a road section, and a frame for positioning a test wheel on the surface of the road section. During operation of the apparatus the test wheel, by a tread thereof, describes a circular path over the road surface. The frame is provided with a sensor for measuring a force exerted on the measuring wheel by the road surface.

12 Claims, 5 Drawing Sheets

TESTING APPARATUS

The invention relates to a testing apparatus, comprising a carrying construction for supporting a road section, and a frame for positioning a test wheel on the surface of the road section, such that during operation of the apparatus the test wheel, by a tread thereof, describes a circular path over the road surface.

Such a testing apparatus is known from, for example, U.S. Pat. No. 4,938,055. In that apparatus, the measuring wheel rides on an annular road section to simulate wear of a type of road surfacing resulting from road traffic. Deformation of the annular road section can be established by inspection after the road section has been loaded by the test wheel for a period of time.

To enable sound investigation on the interaction between road surface and tires of vehicles riding the surface, the need arises to obtain a testing apparatus whereby measurements become available in a systematic manner.

The object of the invention is to provide an improved testing apparatus of the type indicated in the opening paragraph hereof. In particular, the object of the invention is to obtain a testing apparatus according to the opening paragraph hereof that, with preservation of the basic principle of the construction, allows measurements to be generated in a systematic manner. To this end, the frame for positioning the test wheel is further provided with a sensor for measuring a force exerted on the test wheel by the road surface.

By providing the frame with a sensor for measuring the force that the road surface exerts on the test wheel, in a systematic manner measuring data can be obtained for analysis of the interaction between the test wheel and the road surface. Moreover, the measurements can be generated concurrently with the loading of the road surface. Thus, a test of the road surface can be simultaneously combined with investigations on physical changes occurring on the test wheel during the test. Undesirable interruptions during the test can thus be reduced or wholly eliminated.

In this connection, the "force exerted on the test wheel by the road surface" is understood to mean the force buildup which the test wheel experiences from the road. Preferably, all components of the force exerted on the test wheel are determined.

Consequently, a measurement can, in principle, be performed instantaneously, continuously and over the complete driving surface of a road test piece, during the whole testing cycle.

Preferably, the sensor is integrated into the carrying arm, so that a robust and simple construction is obtained for positioning the test wheel and carrying out measurements on the test wheel. With advantage, use is made here of the insight that the force exerted on the test wheel by the road surface is wholly transmitted through the carrying arm, so that deformations on the carrying arm are directly related to the force-to-be-measured on the test wheel.

By positioning the sensor in a local reduction of the carrying arm, relatively slight movements in the carrying arm, such as bending and torsion, can be observed, while the carrying arm as a whole yet forms a firm entity.

In a preferred embodiment according to the invention, the sensor comprises a strain gauge, so that with relatively inexpensive means an accurate measurement of the force on the test wheel can be obtained.

Optionally, the angle of the test wheel axle with respect to the circular path on the road surface is settable. The test wheel can then be oriented such that there is a so-called slip angle. In this way, various practical situations can be simulated, for example, taking a bend. Also, an artificial, accelerated wear of the road surface can be generated.

The invention also relates to a method.

Further advantageous embodiments of the invention are represented in the subclaims.

The invention will be further elucidated on the basis of an exemplary embodiment which is represented in the drawings. In the drawings.

The figure is only a schematic representation of a preferred embodiment of the invention. In the figures, identical or corresponding parts are indicated with the same reference numerals.

Figure 1:
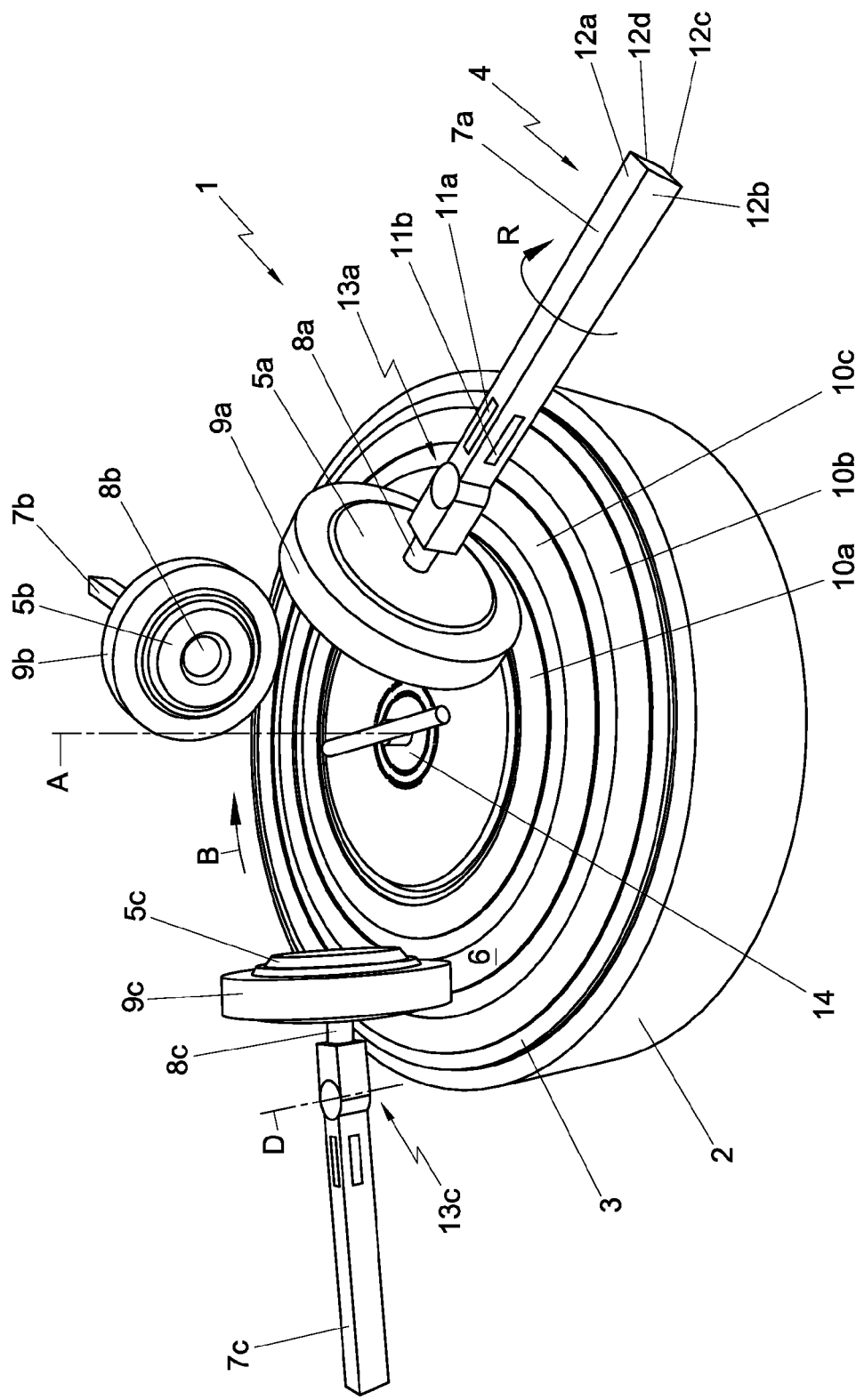
FIG. 1 shows a schematic perspective top plan view of a testing apparatus according to the invention.

FIG. 1 shows an embodiment of a testing apparatus 1 according to the invention. The apparatus 1 has a carrying construction 2 for supporting a road section 3. Also, the apparatus 1 has a partly shown frame 4 for positioning test wheels 5*a-c* on the surface 6 of the road section 3. The frame comprises carrying arms 7*a-c*. On each carrying arm 7 a test wheel 5 is rotatably mounted.

The carrying construction 2 comprises a drive for rotatably driving the road section 3. During operation of the apparatus 1 the road section 3 turns in a rotational direction B about a central axis A. The carrying arms 7 place the test wheels 5, also called measuring wheels, on the road surface 6, so that the wheels 5, through the contact with the road surface, rotate about their axles 8*a-c*. Doing so, the measuring wheels 5, by their treads 9*a-c*, describe circular paths 10*a-c* over the road surface 6. The revolving of the road section simulates the passage of a vehicle over the road. As the measuring wheels 5 each follow their own track on the road surface 6, a relatively large part of the surface 6 can be utilized for testing road surfacing and/or measuring wheel. Moreover, concurrently, different types of measuring wheels can be tested. In addition, the use of a plurality of measuring wheels 5 provides the advantage that the carrying construction 2 is loaded more evenly. In a preferred embodiment according to the invention, the positions of the test wheels are substantially proportionally distributed in the rotational direction B of the road section 3.

The frame 4 for positioning the measuring wheels 5 is furthermore provided with a sensor 11 for measuring a force exerted on a test wheel 5 by the road surface 6. In the embodiment shown, the apparatus 1 comprises a plurality of sensors per wheel 5. By the use of two or more sensors, different orientations of the force exerted on the wheel 5 can be measured. The sensors 11 are integrated into the carrying arms 7. To this end, each carrying arm 7 is provided with one or a plurality of local reductions or recesses 12 in which the sensor 11 is received. The reductions or recesses 12 are so dimensioned that realistic forces that are being exerted on the measuring wheel 5 lead to minimum deformations of the carrying arm adjacent the reduction or recess which are reproducibly measurable with the sensors. Naturally, the carrying arms may also be realized without local reductions or recesses, so that a construction that is simpler to manufacture is obtained.

The extent of deformation of the carrying arm is a measure of the load to which the test wheel is subjected. Accordingly, by measuring the deformation of the carrying arm, the loading on the test wheel can be determined. Thus, an accurate and reliable measurement can be realized, while yet a robust construction is used. In principle, the sensors 11 may be arranged separately, as an alternative embodiment to an integration into the carrying arm. By arranging a plurality of sensors 11a-b at different positions in a circumferential direction R about a carrying arm 7, an adjustment of the carrying arm 7 can be measured in different orientations. In the embodiment shown, the carrying arm 7 in cross section has a substantially rectangular profile. On each of the four profile parts 12a-12d a sensor 11 is arranged. In FIG. 1 two sensors 11a-b are visible in the carrying arm 7a at the front, right.

The sensors each comprise a strain gauge. Naturally, other embodiments of force sensors are also applicable. Furthermore, accuracy and reliability of the force measurement can be raised considerably by periodically calibrating the sensors.

The sensors make a continuous, ongoing and at the same time accurate measurement possible, while a good signal-to-noise ratio can be achieved, both of the vertical force component to be registered and of the horizontal force components to be registered.

It is noted that the sensors may also be arranged at different locations on the frame, for example, on a junction between the carrying arms and a central coupling piece. Furthermore, the sensors may be positioned and/or oriented in a different manner, for example, arranged on the same profile part 12a-d, but with a mutually different orientation.

The carrying arms 7 are provided with a hinge element 13a,c for pivoting the axis 8 of the measuring wheel 5 about a pivoting axis D, see the left-hand carrying arm 7c in FIG. 1, with respect to the circular path 10 at the road surface 6. Thus, the angle of the test wheel axis 8 is settable with respect to an instantaneous direction of movement of the test wheel 5.

Furthermore, the wheels 5 are preferably detachably mounted to the carrying arms, so that replacement by other specimens can easily be carried out.

Figure 2:
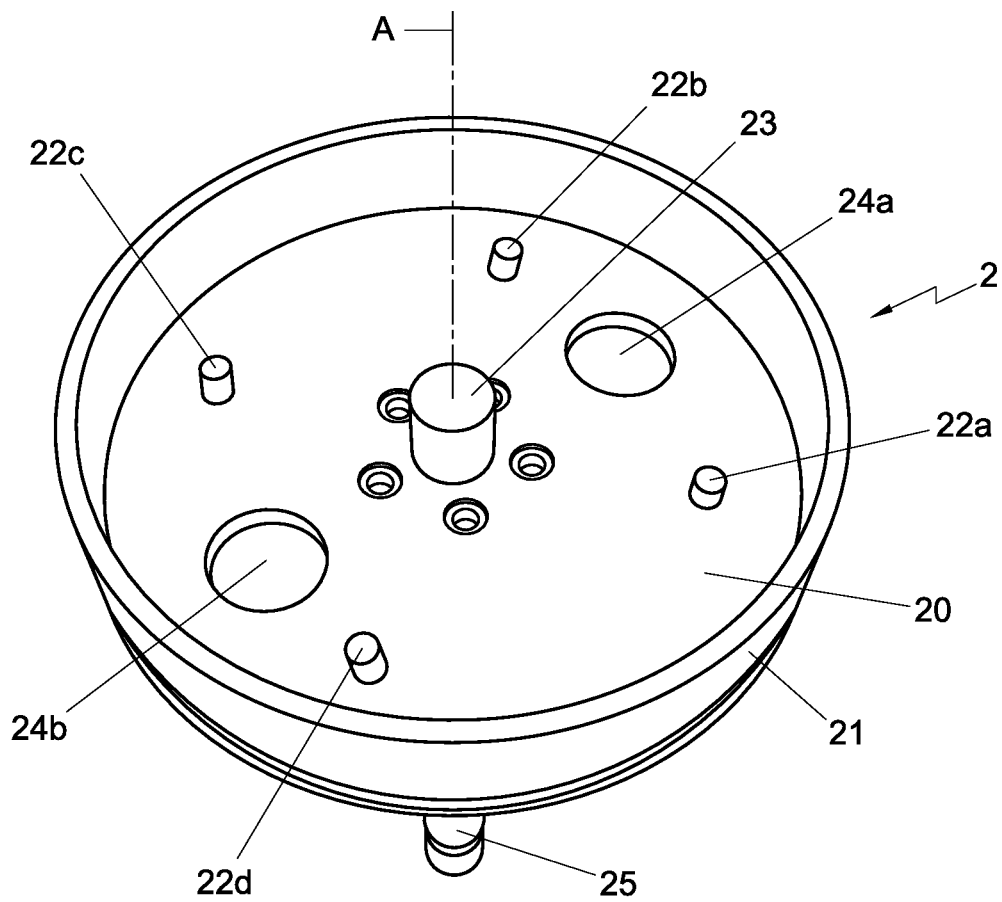
FIG. 2 shows a schematic perspective top plan view of a carrying construction of the testing apparatus of FIG. 1.

FIG. 2 shows a schematic perspective top plan view of a carrying construction 2 of the testing apparatus 1. The carrying construction 2 comprises a turntable 20, rotatable about the central axis A and having an upstanding edge 21, for receiving a road section 3. Through the construction with the upstanding edge 21, a cavity is formed, so that the received road section 3 can be confined in circumferential direction. Preferably, the road section 3 is detachably arranged as a separate module on the carrying construction 2. Owing to the modular structure, the road section 3 can easily be replaced by another specimen after a test. Also, the testing apparatus 1 is thus flexibly deployable for different kinds of road sections.

By great preference, the road section 3 is substantially disk-shaped, so that the section can easily be received on the turntable 20. By virtue of the disk shape, advantageously, the road surface 6 can be optimally utilized during rotation of the disk. However, in principle, a different type of geometry is applicable, for example, a square section.

The turntable 20 is provided with supporting points 22a-d for supporting the discrete road section 3. Furthermore, the turntable 20 comprises a central attachment point 23 by which the road section 3 can be secured to the turntable 20. FIG. 1 shows a central nut 14 which cooperates with the central attachment point 23 for locking retention of the road section 3. It will be clear to those skilled in the art that also other attachment constructions may be used. Optionally, the turntable 20 is provided with one or a plurality of openings 24a,b for pushing up a road section 3 to be removed. Furthermore, the turntable 20 is mounted on a central driving shaft 25 for driving the turntable 20 for rotation.

Figure 3:
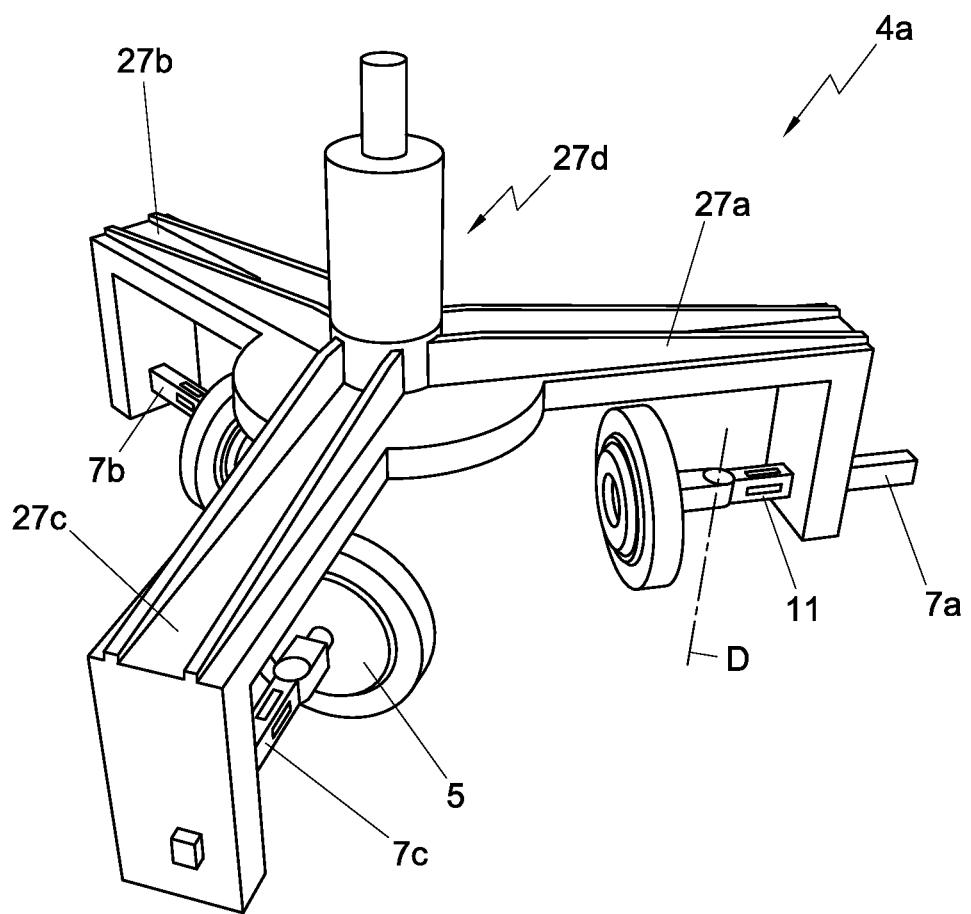
FIG. 3 shows a schematic perspective top plan view of a first frame part for positioning test wheels in the apparatus of FIG. 1.

FIG. 3 shows a schematic perspective top plan view of a first frame part 4a for positioning the test wheels 5. The carrying arms 7a-c are mounted on a star-shaped frame element having three arms 27a-c which extend radially from a central part 27d. The central part forms a common central coupling piece which can be detachably mounted to a pressure frame. Preferably, the coupling piece 27d comprises a pressure sensor for measuring a static pressure which is exerted on the wheels via the pressure frame. Also, the coupling piece may be provided with a homokinetic coupling, thereby allowing correction for a difference in diameter of the individual wheels.

Figure 4:
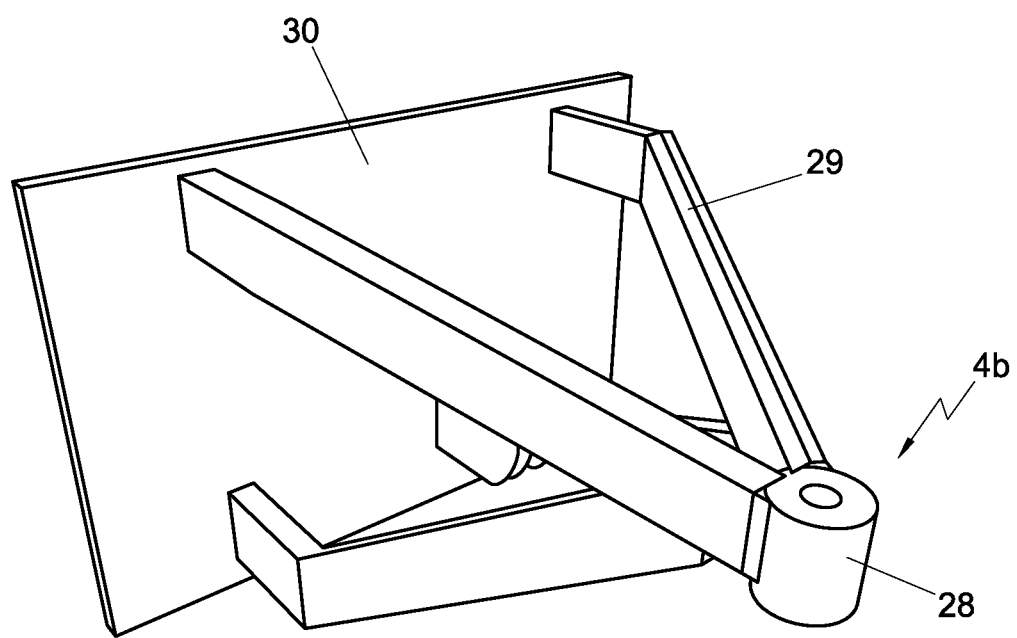
FIG. 4 shows a schematic perspective top plan view of a second frame part for positioning test wheels in the apparatus of FIG. 1.

FIG. 4 shows a schematic perspective top plan view of a second frame part 4b for positioning the test wheels 5. The second frame part 4b forms a pressure frame for pressing the wheels 5 onto the road surface 6. The pressure frame 4b comprises a coupling part 28 for coupling with the coupling piece 27d of the first frame part 4a, and a frame structure 29 which connects the coupling part 28 with a plate 30. The plate may be anchored, but preferably in such a way as to allow an adjustment in substantially vertical direction, for example, with a vertical guide rail construction. Furthermore, the coupling part 28 is preferably adjustable in the substantially horizontal plane, so that the coupling part can be positioned straight above the central axis A of the carrying construction 2 of the road section 3.

By the use of a modular, detachable structure, individual parts can easily be exchanged. Especially regarding parts that are subject to relatively high wear, this provides advantages, because the testing apparatus is thus rendered highly deployable and offers a high flexibility with regard to different types of road sections and test wheels.

Figure 5:
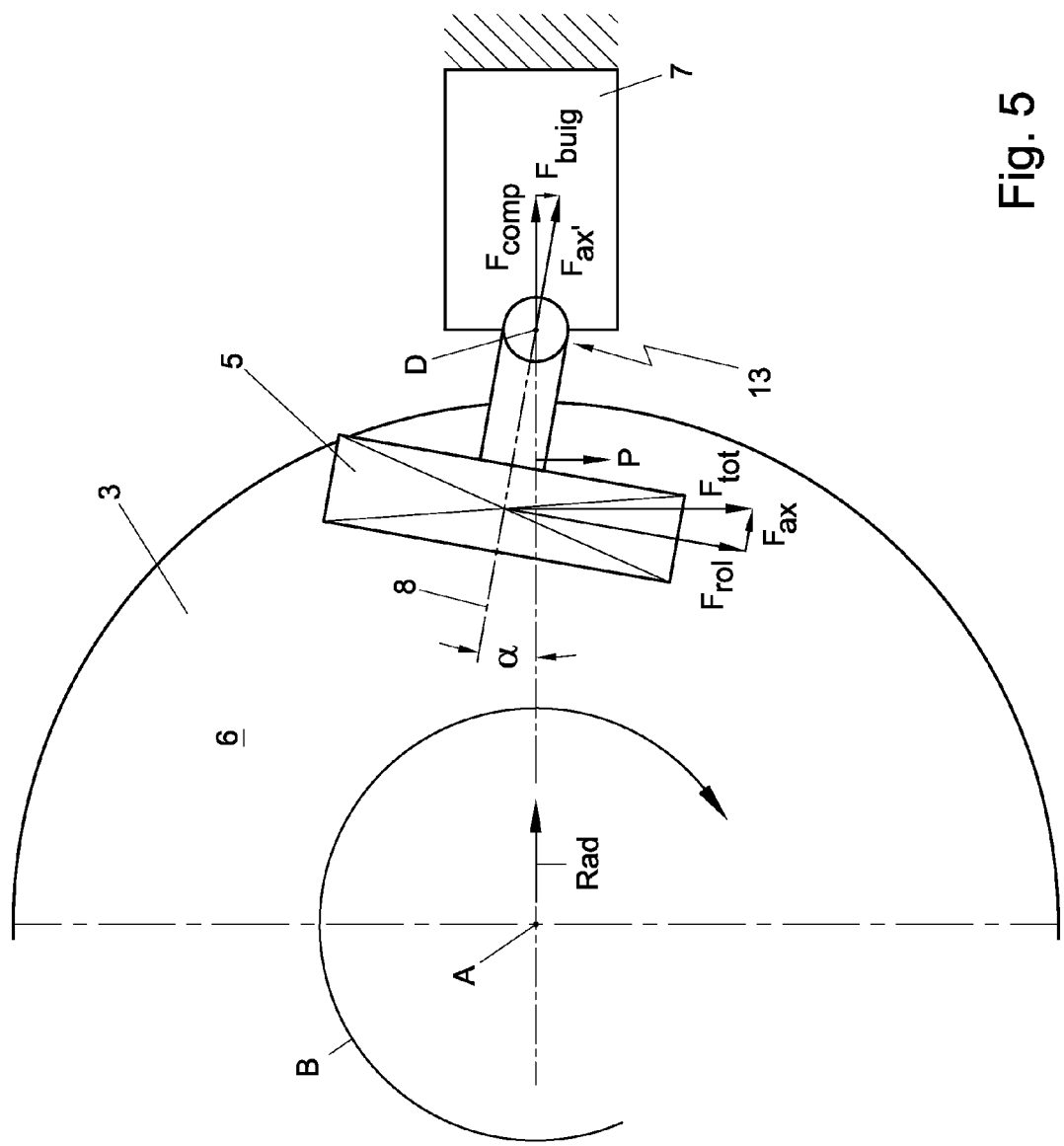
FIG. 5 shows a schematic top plan view of a test wheel in the testing apparatus of FIG. 1.

FIG. 5 shows a schematic top plan view of a test wheel 5 in the testing apparatus 1 of FIG. 1. The test wheel 5 is positioned on the road surface 6 of a road section 3 at a preferably infinitely variable angle with respect to the path that the test wheel 5 travels on the circular track of the road surface. The wheel 5 is placed slightly obliquely with respect to the local direction of travel of the wheel 5 with respect to the road surface 6. Thus the axis 8 of the wheel 5 makes a small angle α of about 10° with respect to the local radial direction Rad from the central axis A of the carrying construction 2. Through the oblique arrangement of the wheel 5, slip arises. The force $F_{tot}$ exerted by the road surface 6 on the wheel in horizontal direction comprises a pure rolling force component $F_{rol}$ and an axial force component $F_{ax}$. Adjacent the sensors in the carrying arm 7, this results in a second axial force $F_{ax'}$, which is built up from a compression force $F_{comp}$ and a bending force $F_{buig}$. Thus, from the measured forces in the carrying arm, the force buildup which the wheel 5 experiences from the road surface 6 can be derived.

The testing apparatus can be used as a relatively compact and robust machine for simulating all sorts of practical circumstances of a road surface. Thus, the road segment may be tested dry or wet, possibly at different water film levels, and at various temperatures. The apparatus is deployable for carrying out measurements on a variety of types of road surfacing, for example, asphalt, concrete and paving bricks, as well as on rubber mixtures of car and truck tires. Thus, diverse parameters may be investigated, for example, skid resistance, course of skid resistance per vehicle passage, rutting, course of rutting per vehicle passage, fraying, and rate of rubber wear.

By placing the wheels obliquely, as described above, and by placing the wheels on the road surface with a particular pressure, at the same time the skid resistance and the interplay of forces in the contact interface between wheel and road surface can be measured. The extent of rutting may be determined by a separate measurement, whereby preferably the height of the whole testable surface up to the road surfacing is scanned, for example, with the aid of a laser measurement. Also fraying of the road surface can thus be determined. Furthermore, a rubber wear rate can be determined by correlating the amount of worn-off rubber of tires fitted on the measuring wheels to the number of revolutions of the road section.

The testing apparatus can be operated safely, remotely and simply, while reliable measurements can be obtained simultaneously. The elegant use of the force sensors allows an accurate and reliable three-dimensional force determination in the contact surface between the test wheels and the road surface. Both horizontal and vertical forces can be measured. Also torsional and shearing forces can be determined. Furthermore, the measurement is in principle independent of the extent of wear in rubber and/or surfacing surface.

The invention is not limited to the exemplary embodiments described here. Many variants are possible.

Instead of a singular carrying arm, the frame may comprise a different component for rotatably mounting a test wheel. Thus, the frame can comprise a sheet metal work or a subframe having a plurality of segments, to which the test wheel is attached.

Furthermore, the testing apparatus 1 can comprise a different number of test wheels 5, such as more than three test wheels, for example, four or more test wheels, or fewer than three test wheels, for example, two test wheels or just one test wheel.

In use of the testing apparatus according to the invention, the wheels roll over the road surface of the road section. For inducing the rolling movement, the turntable turns about the central axis. In an alternative embodiment, the wheels are driven for rotation and the turntable stands still. The embodiment described with reference to the drawing is advantageous in that not only a simpler construction is obtained but also the moving parts can be screened better, which promotes safety. It is noted that also a combination of the two principles is possible, whereby both the turntable and the frame carrying the wheels rotate.

Also, optionally, the force that the test wheel exerts on the surface of the road section, at least a component thereof, for example, a vertical component, may be set. In this way, a real, settable axle pressure can be simulated. On the basis of the vertical force exerted on the test wheel, which is determined with the sensor measurement, a feedback loop may be realized for the force by which the test wheel is pressed onto the road surface. The value of the measured vertical force is then compared with a preset value. Based on the comparison, the force exerted via the test wheel on the road section can be adapted. In this way, a constant axle pressure can be simulated, independently of wear and/or deformation of the road surfacing and/or of the test wheel.

In addition, the testing apparatus may be provided with units that influence the physical properties of the road section. Such units may comprise, for example, a moisturizing installation and/or a freezing installation. Thus, meteorological conditions can be imitated.

Such variants will be clear to those skilled in the art and are understood to be within the scope of the invention, as set forth in the following claims.

The invention claimed is:

1. A testing apparatus, comprising a carrying construction for supporting a road section, and a frame for positioning a test wheel on the surface of the road section, such that during operation of the apparatus the test wheel, by a tread thereof, describes a circular path over the road surface, wherein the frame comprises a carrying arm to which the test wheel is rotatably mounted, said testing apparatus comprising a sensor integrated into the carrying arm for measuring the deformation of the carrying arm for determining a force exerted on the test wheel by the road surface.

2. The testing apparatus according to claim 1, wherein the carrying construction comprises a turntable rotatable about a central axis.

3. The testing apparatus according to claim 1, furthermore comprising a road section which is detachably arranged as a separate module on the carrying construction.

4. The testing apparatus according to claim 1, wherein the road section is substantially disk-shaped.

5. The testing apparatus according to claim 1, wherein the sensor comprises a strain gauge.

6. The testing apparatus according to claim 1, wherein the sensor is positioned in a local reduction of the carrying arm.

7. The testing apparatus according to claim 1, furthermore comprising at least two sensors which are arranged at different positions in circumferential direction around the carrying arm for measuring deformations of the carrying arm in different orientations for determining force components in different orientations exerted on the test wheel.

8. The testing apparatus according to claim 1, wherein an angle of the test wheel axis relative to the circular path on the road surface is adjustable.

9. The testing apparatus according to claim 1, wherein the frame comprises a plurality of carrying arms, each for carrying a test wheel.

10. The testing apparatus according to claim 9, wherein the test wheels each follow a track of their own on the road surface.

11. The testing apparatus according to claim 9, wherein the carrying arms are detachably mounted on a pressure frame via a common central coupling piece.

12. The testing apparatus according to claim 11, wherein the common central coupling piece comprises a homokinetic coupling.

* * * * *